(12) United States Patent
Buenafe

(10) Patent No.: US 10,039,891 B2
(45) Date of Patent: Aug. 7, 2018

(54) SYSTEM FOR ALARM-MONITORING PATIENTS ON CONTINUOUS FREE FLOW OXYGEN DELIVERY VIA T-PIECE ON CLOSED TRACHEAL SUCTION SYSTEM

(71) Applicant: Edrine Pineda Buenafe, Winnetka, CA (US)

(72) Inventor: Edrine Pineda Buenafe, Winnetka, CA (US)

(*) Notice: Subject to any disclaimer, the term of this patent is extended or adjusted under 35 U.S.C. 154(b) by 554 days.

(21) Appl. No.: 14/645,028

(22) Filed: Mar. 11, 2015

(65) Prior Publication Data
US 2015/0306323 A1     Oct. 29, 2015

Related U.S. Application Data

(60) Provisional application No. 61/951,419, filed on Mar. 11, 2014.

(51) Int. Cl.
| | |
|---|---|
| *A61M 16/00* | (2006.01) |
| *A61M 16/04* | (2006.01) |
| *A61M 16/08* | (2006.01) |
| *A61M 39/10* | (2006.01) |
| *H01F 7/02* | (2006.01) |
| *H01H 45/00* | (2006.01) |

(52) U.S. Cl.
CPC .... *A61M 16/0051* (2013.01); *A61M 16/0057* (2013.01); *A61M 16/021* (2017.08); *A61M 16/0402* (2014.02); *A61M 16/0833* (2014.02); *A61M 39/1055* (2013.01); *A61M 2039/1022* (2013.01); *A61M 2205/14* (2013.01); *A61M 2205/3592* (2013.01)

(58) Field of Classification Search
CPC .............. A61M 2039/0267; A61M 2039/1005
See application file for complete search history.

(56) References Cited

U.S. PATENT DOCUMENTS

| | | | | |
|---|---|---|---|---|
| 3,595,228 A | * | 7/1971 | Simon ............... | A61M 16/0051 128/202.22 |
| 4,067,329 A | * | 1/1978 | Winicki ............ | A61M 16/0051 128/202.22 |
| 4,485,822 A | * | 12/1984 | O'Connor .............. | A61B 5/097 128/207.17 |
| 5,320,092 A | * | 6/1994 | Ryder ............... | A61M 16/0666 128/202.22 |
| 5,405,336 A | * | 4/1995 | Austin .............. | A61M 25/0014 604/534 |
| 5,626,129 A | * | 5/1997 | Klimm .............. | A61M 16/0051 128/202.22 |

(Continued)

*Primary Examiner* — (Jackie) Tan-Uyen T Ho
*Assistant Examiner* — Joseph D Boecker
(74) *Attorney, Agent, or Firm* — Brooks Acordia IP Law, PC; Pejman Yedidsion

(57) ABSTRACT

An endotracheal tube alarm apparatus includes an inner cannula having an outer mating surface, the outer mating surface having a seated first electrical conductor, and a ventilator tube having an inner mating surface slidably coupled to the outer mating surface of the inner cannula, the inner mating surface having seated second and third electrical conductors extending circumferentially about the inner mating surface and each in complementary opposition to the first electrical conductor so that the third electrical conductor is in electrical communication with the second electrical conductor through the first electrical conductor.

10 Claims, 5 Drawing Sheets

(56) References Cited

U.S. PATENT DOCUMENTS

| | | | | |
|---|---|---|---|---|
| 6,851,427 B1* | 2/2005 | Nashed | ............ | A61M 16/0051 128/204.18 |
| 6,874,502 B1* | 4/2005 | Nashed | ............ | A61M 16/0051 128/202.27 |
| 8,800,552 B2* | 8/2014 | Burns | ................ | A61M 16/04 128/200.24 |
| 9,101,728 B1* | 8/2015 | Al-Wazzan | ....... | A61M 16/0488 |
| 2007/0179473 A1* | 8/2007 | Masters | ............ | A61M 25/0097 604/533 |
| 2007/0277828 A1* | 12/2007 | Ho | ...................... | A61M 16/08 128/206.21 |
| 2008/0041391 A1* | 2/2008 | Worley | ............ | A61M 16/0465 128/207.14 |
| 2008/0078388 A1* | 4/2008 | Vandine | ............... | A61M 16/04 128/204.21 |
| 2008/0265191 A1* | 10/2008 | Walborn | ............... | A61M 39/26 251/129.01 |
| 2011/0102168 A1* | 5/2011 | Mariman | ............... | A01C 7/082 340/451 |
| 2013/0345587 A1* | 12/2013 | Colman | ............ | A61M 39/1011 600/532 |
| 2015/0013684 A1* | 1/2015 | Sethiya | ............ | A61M 16/0468 128/207.15 |
| 2015/0083122 A1* | 3/2015 | Velez-Rivera | .... | A61M 16/0816 128/202.22 |
| 2015/0306365 A1* | 10/2015 | Besko | ................ | A61M 39/10 604/111 |
| 2016/0230914 A1* | 8/2016 | Roy | ..................... | A61M 39/00 |

* cited by examiner

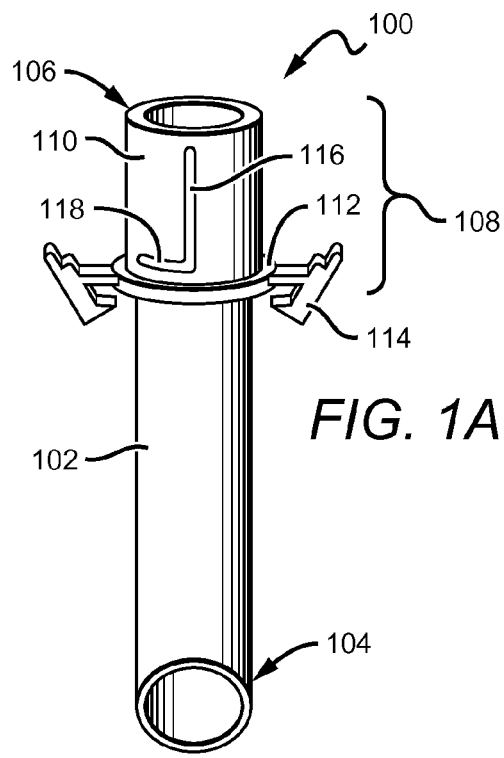
FIG. 1A
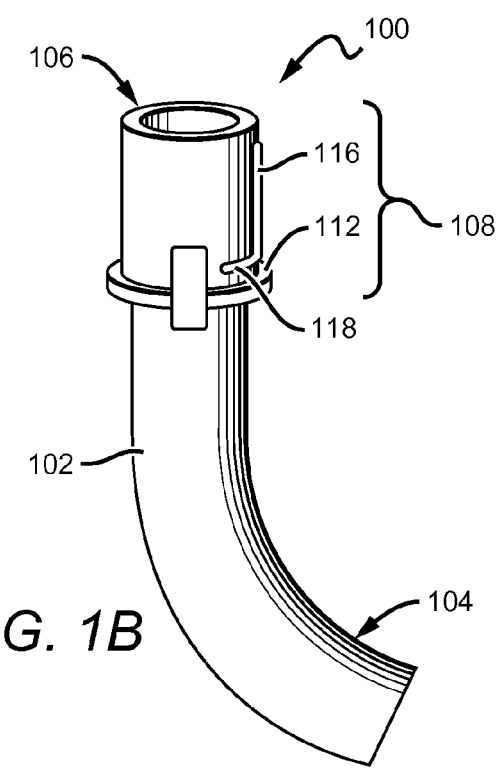
FIG. 1B
FIG. 2A
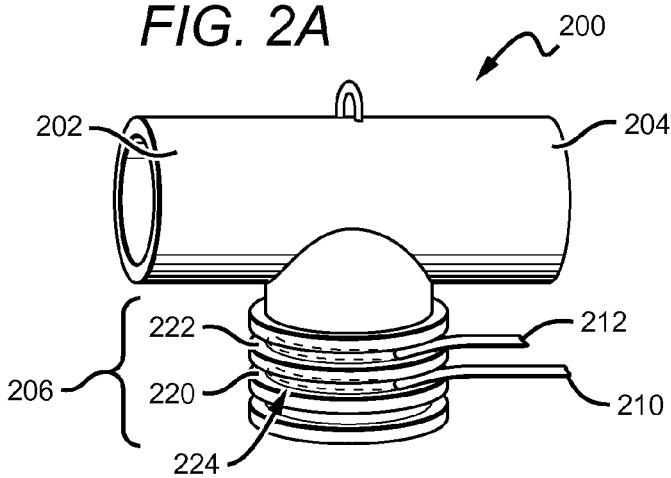
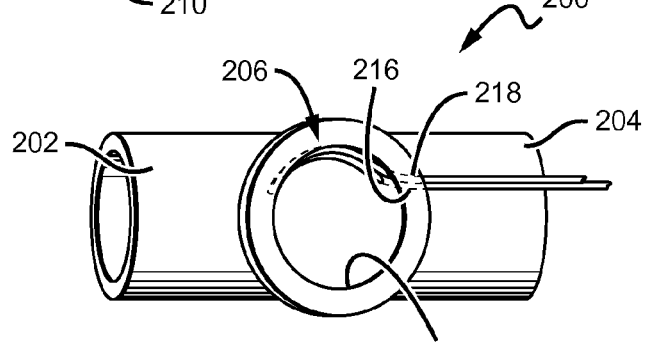
FIG. 2B

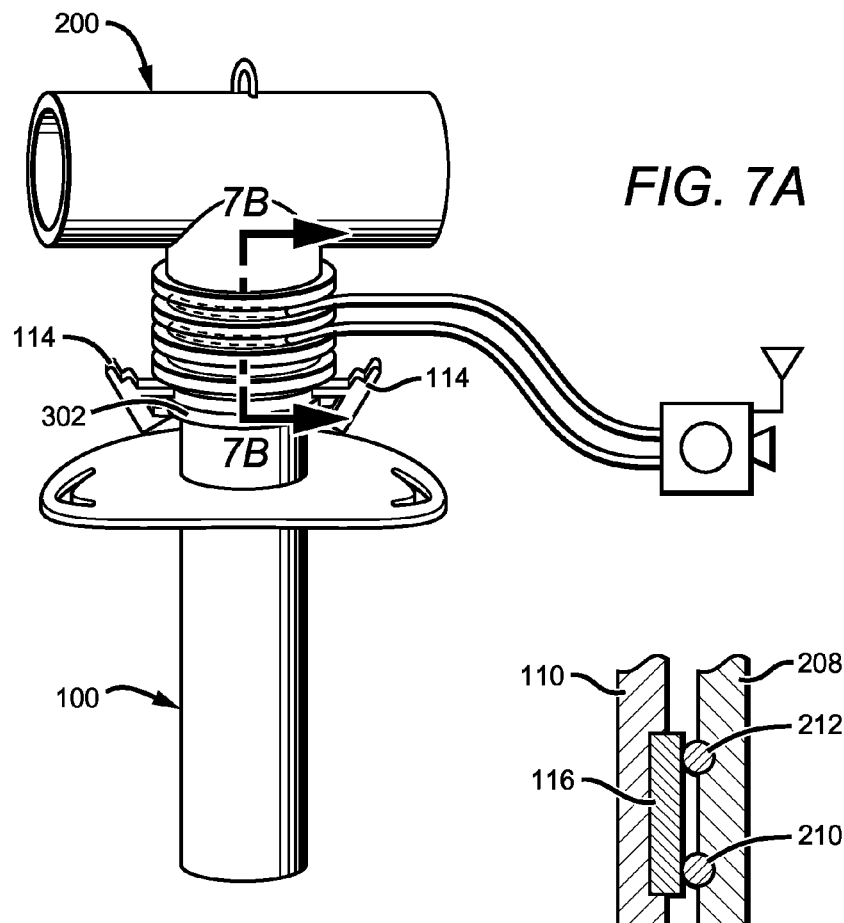
FIG. 7A
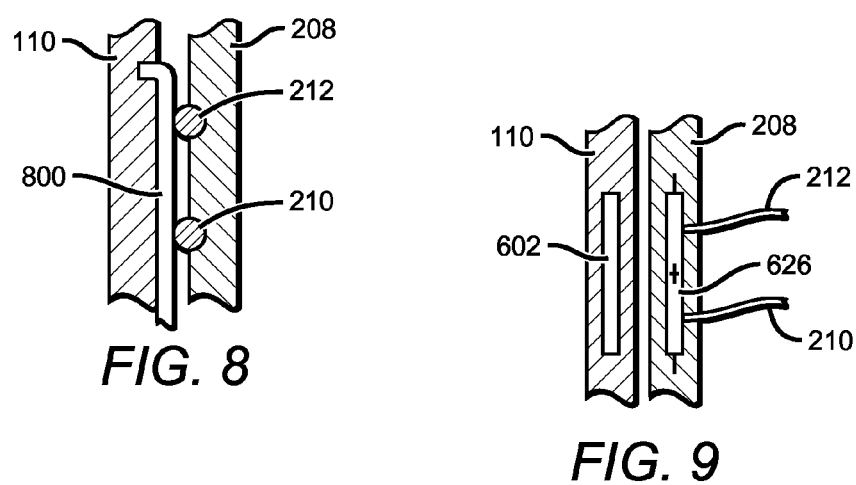
FIG. 7B
FIG. 8
FIG. 9

SYSTEM FOR ALARM-MONITORING PATIENTS ON CONTINUOUS FREE FLOW OXYGEN DELIVERY VIA T-PIECE ON CLOSED TRACHEAL SUCTION SYSTEM

CROSS-REFERENCE TO RELATED APPLICATIONS

This application claims the benefit of U.S. Provisional Application No. 61/951,419 filed Mar. 11, 2014, the disclosure of which is hereby incorporated by reference in its entirety for all purposes.

BACKGROUND

Field of the Invention

The invention relates to free flow oxygen delivery systems, and more particularly to oxygen delivery systems used for trached or intubated patients on continuous oxygen via T-piece.

Description of the Related Art

Every year, hundreds of patients, trached or intubated and on continuous oxygen via a T-piece or closed tracheal suction adapters are accidentally disconnected for one reason or another. Most of these patients on this modality are usually in the process of weaning off of a mechanical ventilator, and most are dependent on higher oxygen concentrations, have weakened respiratory musculature, and, if alert, are highly anxious. In most cases, an accidental disconnection will result in severe respiratory distress due to hypoxia. This could also precipitate acute secondary conditions like a myocardial infarction, stroke, and even death.

SUMMARY

An exemplary endotracheal tube alarm apparatus may have an inner cannula having an outer mating surface, the outer mating surface having a seated first electrical conductor; and a ventilator tube having an inner mating surface slidably coupled to the outer mating surface of the inner cannula, the inner mating surface having seated second and third electrical conductors extending circumferentially about the inner mating surface and each in complementary opposition to the first electrical conductor; where the third electrical conductor may be in electrical communication with the second electrical conductor through the first electrical conductor. In additional apparatus embodiments, the second and third electrical conductors may extend through a sidewall of the ventilator tube. Additional apparatus embodiments may have an alarm in communication with the first and second conductors, and the alarm may be in communication with the first and second conductors through a wireless transmitter. In additional apparatus embodiments, the alarm may be configured to trigger when the second and third electrical conductors are not in electrical communication through the first electrical conductor. In additional apparatus embodiments, the ventilator tube may be a T-piece; a swivel connector; and/or a flex-adapter tube. In additional apparatus embodiments, the flex-adapter tube may have an outer mating surface having a seated fourth electrical conductor. Additional apparatus embodiments may have a tracheal T-piece having an inner mating surface slidably coupled to the outer mating surface of the flex-adapter; and fifth and sixth electrical conductors may be seated in the inner mating surface; where the sixth electrical conductor may be in electrical communication with the fifth electrical conductor through the fourth electrical conductor.

In additional apparatus embodiments, the first electrical conductor may be selected from the group consisting of a metallic wire, a metallic clip, a metallic strip, and metallic tape.

Exemplary tracheostomy tube alarm apparatus embodiments may have an inner cannula having an exterior circumferential ventilator tube mating surface and an electrical conductor embedded in the exterior circumferential ventilator tube mating surface; a ventilator tube seated on the ventilator tube mating surface; and a detector in communication with the electrical conductor through a sidewall of the ventilator tube. In additional apparatus embodiments, the ventilator tube may have a tracheal T-piece. In additional apparatus embodiments, the ventilator tube may be a flex-adapter tube. In additional apparatus embodiments, the electrical conductor may be a magnet. In additional apparatus embodiments, the detector may be a magnetic switch. In additional apparatus embodiments, the detector may be a Hall Effect sensor.

Exemplary inner cannula apparatus embodiments may have a first electrical conductor seated in an outer surface of an inner cannula; and second and third electrical conductors seated in an inner circumferential surface of a ventilator tube, the ventilator tube may be seated on the outer surface of the inner cannula; where the second electrical conductor may be in electrical communication with the third electrical conductor through the first electrical conductor.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which:

FIG. 1A depicts a front perspective view of an embodiment of an inner cannula having a seated first conductor as part of an endotracheal tube alarm system;

FIG. 1B depicts a side perspective view of the embodiment of the inner cannula of FIG. 1A having a flexible endotracheal portion at its distal end that curves longitudinally to form a partial J shape;

FIG. 2A depicts a side perspective view of an embodiment of a T-piece ventilator tube having embedded conductors;

FIG. 2B depicts a bottom perspective view of the embodiment of the T-piece of FIG. 2A having channels to seat the embedded connectors;

FIG. 7A depicts a front perspective view of an embodiment of a ventilator tube in the form of a T-piece seated on an exterior circumferential ventilator tube mating surface of an inner cannula;

FIG. 7B depicts a cross-sectional view along the line 7B-7B in FIG. 7A;

FIG. 8 depicts a cross-sectional view of an embodiment of a ventilator tube having first and second electrical conductors in complementary opposition and in electrical communication with a metal bracket; and FIG. 9 depicts a cross-sectional view of an embodiment of a ventilator tube having an embedded magnet and a Hall effect sensor.

DETAILED DESCRIPTION

Figure 3:
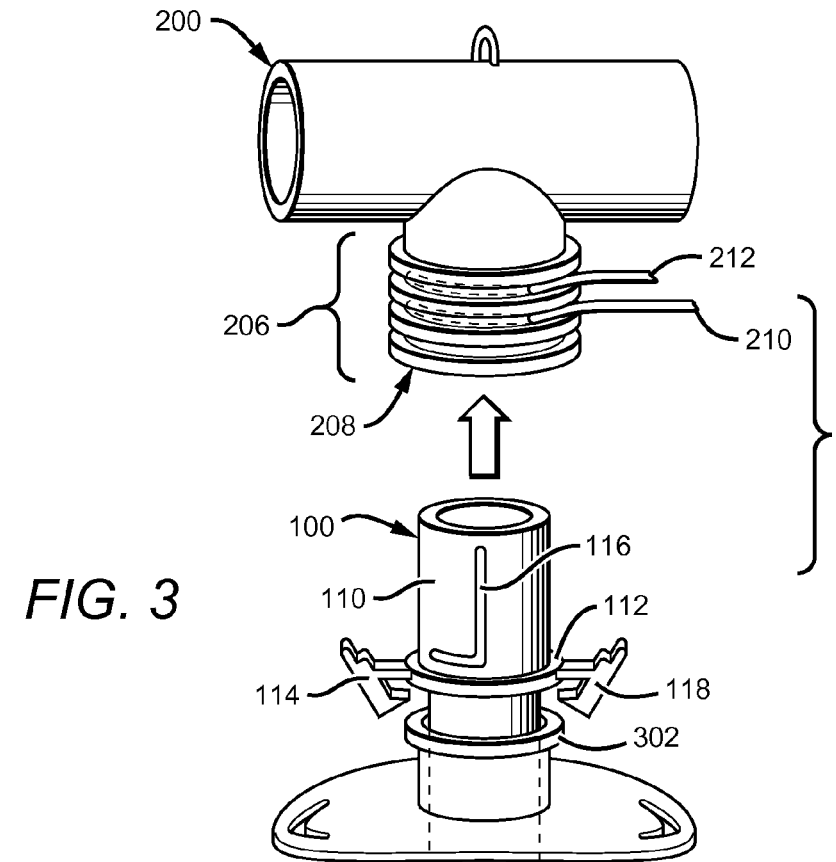
FIG. 3 depicts an exploded perspective view of the inner cannula of FIGS. 1A-1B assembled with an outer cannula and the T-piece of FIGS. 2A-2B having electrical conductors.

FIGS. 1A and 1B are front and side perspective views, respectively, of one embodiment of an inner cannula that has a seated first conductor as part of an endotracheal tube alarm system for use with medical patient intubation. The inner cannula 100 has a flexible endotracheal portion 102 at its distal end 104 that curves longitudinally to form a partial J shape for easier insertion into a rigid outer cannula (see FIG. 3) having the same or similar J shape. At its proximal end 106, the inner cannula 100 has a coupler portion 108 that may have a circumferential and substantially rigid outer mating surface 110. A collar 112 may extend circumferentially and away from the remainder of the coupler portion 108 to provide an insertion stop to abut the rigid outer cannula (see FIG. 3) when assembled. A locking mechanism such as rotatable clasps 114 may extend from the coupler portion 108 or from the collar 112 of the coupler portion 108 on opposite sides of the inner cannula 100. The flexible endotracheal portion 102, coupler portion 108, collar 112, and locking mechanism 114 may be configured in the form of a Shiley™ brand inner cannula such as that offered by Covidien corporation of Minneapolis, Minn.

An electrical conductor 116 may be formed with or otherwise coupled to the outer mating surface 110 and may be configured so that a portion of the electrical conductor 116 extends out from the outer mating surface 110. In one embodiment, the electrical conductor 116 may be a seated steel wire that partially extends from the outer mating surface 110. The electrical conductor 116 is illustrated extending generally longitudinally along the outer mating surface 108 between the distal and proximal ends (104, 106) and having a perpendicular axial component 118 so that the electrical conductor forms an "L" shape. In other embodiments, the electrical conductor 116 may extend generally longitudinally and may form a "U" shape, a "V" shape, or may extend linearly. In other embodiments, the electrical conductor 116 may be a seated metallic clip. In further embodiments, the electrical conductor may be a metal strip or metal tape that is seated on the outer mating surface 110.

As used herein, "seated" may mean seated at a top surface such as with an adhesive, partially embedded, or fully embedded within the described material such as may result from an injection molded process. For example, an embedded electrical conductor that has a circular cross section may be seated on the outer mating surface 110 such that ¼ or ¾ of its diameter extends out from the outer mating surface 110 as configured during an injection molding process. In another embodiment, the electrical conductor may be fully seated within the outer mating surface 110 such that none of the conductor actually extends above the outer mating surface 110, but rather an outer surface of the electrical conductor is exposed at the surface of the outer mating surface 110 for contact with another electrical conductor. Also, the electrical conductor may be seated and entirely enveloped by the outer mating surface 110 so that the electrical conductor is insulated from the external environment for use with a Hall effect sensor (see below).

FIGS. 2A and 2B are side perspective and bottom perspective views, respectively, of one embodiment of a ventilator tube in the form of a T-piece having embedded second and third conductors, with the T-piece designed to couple with the inner cannula first illustrated in FIGS. 1A-1B as part of the endotracheal tube alarm system. The T-piece 200 has first and second cylindrical arms 202, 204 that are in internal liquid communication with each other, and are each in internal liquid communication with a shank portion 206. The shank portion 206 has an inner mating surface 208 that is preferably circumferential and may have an inner diameter that approximates an outer diameter of the outer mating surface 110 of the inner cannula 100 to enable the inner mating surface 208 to slidably accept the outer mating surface 110 of the inner cannula 110 (See FIG. 3). The second and third electrical conductors (210, 212) may each be circumferentially seated with the inner mating surface 208. The conductors (210, 212) may extend through an inner sidewall of the shank portion 206, such as through respective holes (216, 218) in the shank 206, for receipt and guidance by respective channels (220, 222) that are formed in an outer surface 224 of the shank portion 206. The second and third electrical conductors (210, 212) may extend to a normally closed circuitry commonly found in typical alarm systems or may extend to electrical conductor terminals (see FIG. 4).

FIG. 3 is an exploded perspective view of the T-piece 200 and inner cannula 100 first illustrated in FIGS. 1A, 1B, 2A, and 2B as assembled with an outer cannula as part of the endotracheal tube alarm system. An outer cannula 300 may be positioned within the trachea of an intubated human patient and may be configured to slidably receive the inner cannula 100. As the inner cannula 100 is slidably seated within the outer cannula 300, the rotatable clasps 114 may slide over and lockably engage with a collar 302 of the outer cannula 300 so that the collar 112 of the inner cannula 100 locks onto the collar 302 of the outer cannula 300 as the collars (112, 302) abut one another. The inner mating surface 208 of the shank portion 206 of the T-piece 200 may slidably receive the outer mating surface 110 of the inner cannula 100. Upon insertion, the electrical conductor 116 seated with the inner mating surface 208 may be in electrical communication with both the second and third electrical conductors (210, 212) to indicate to an alarm in communication with the assembly that the T-piece 200 is connected to the inner cannula 100.

Figure 4:
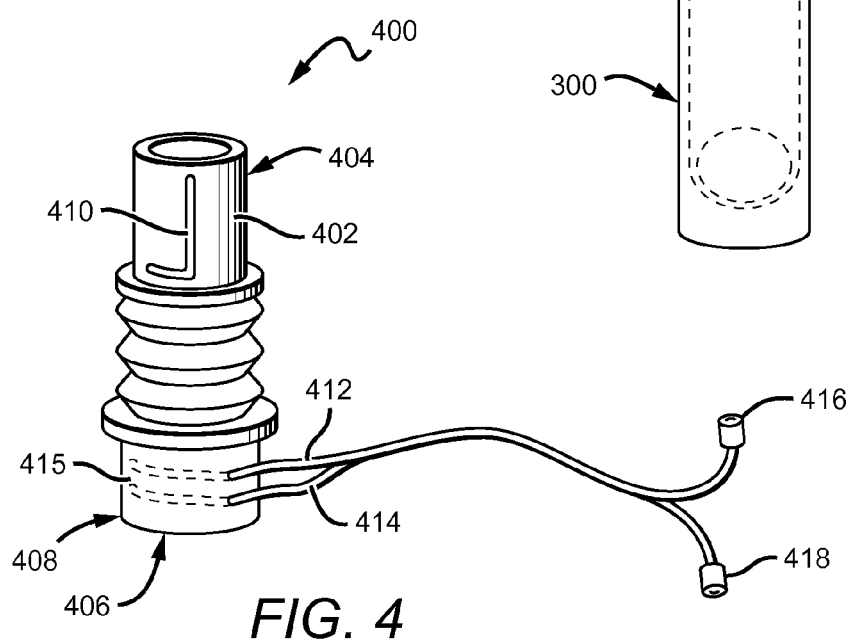
FIG. 4 depicts a front perspective view of an embodiment of a flex adapter tube having an electrical conductor and a pair of wires.

FIG. 4 is a front perspective view of one embodiment of a ventilator tube in the form of a flex adapter tube that has an electrical conductor for use as part of the endotracheal tube alarm system. The flex adapter tube 400 may have an outer mating surface 402 at a proximal end 404, and an inner mating surface 406 at a distal end 408. An electrical conductor 410 may be formed with or otherwise coupled to the outer mating surface 402 and may be configured so that an outer surface of the electrical conductor 410 rises above the local plane of the outer mating surface 402 to enable electrical coupling with another electrical conductor (not shown). In one embodiment, the electrical conductor 410 may be a seated steel wire that extends substantially longitudinally from the proximal end 404 toward the distal end 408 along the outer mating surface 402. In another embodiment, the electrical conductor may be a seated metallic clip, metal strip, metal tape, or other conductive material. In a further embodiment, the electrical conductor 410 may be a magnet and a pair of wires (412, 414) may terminate in either a magnetic switch or a Hall effect sensor to detect the presence or absence of an adjacent magnet.

The pair of wires (412, 414) may extend through a sidewall 415 of the distal end 408 for circumferential seating about the inner mating surface 406. The wires (412, 414) may be terminated at alarm terminals or contacts (416, 418).

Figure 5:
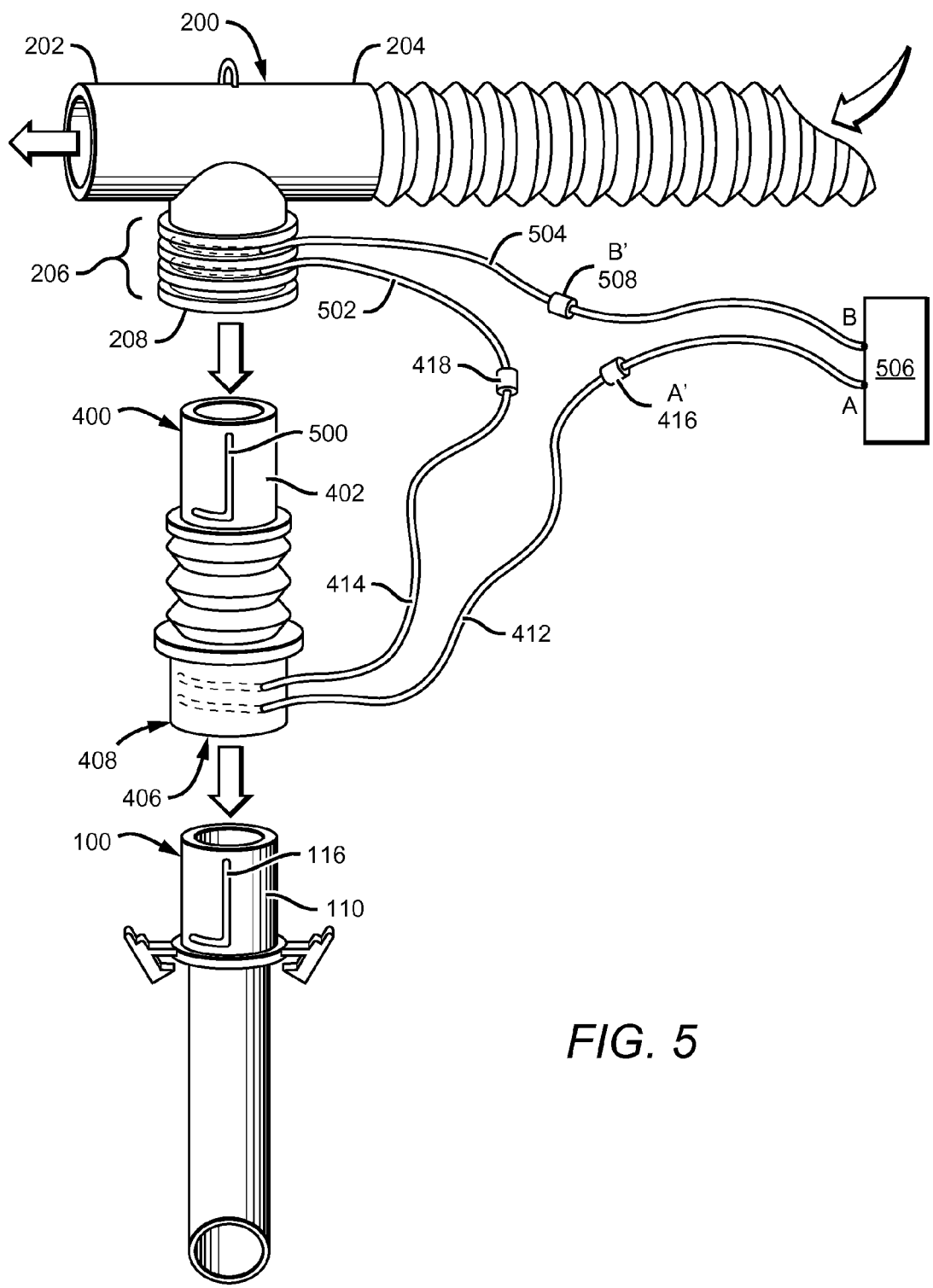
FIG. 5 depicts an exploded perspective view of an embodiment of an endotracheal tube alarm apparatus having the T-piece of FIGS. 2A-2B, the flex adapter tube of FIG. 4, and the inner cannula of FIGS. 1A-1B.

FIG. 5 is an exploded view of one embodiment of an endotracheal tube alarm apparatus for use with a T-piece, flex adapter tube, and inner cannula. A first electrical conductor 116 may be seated on the outer mating surface 110 of the inner cannula 100, with the outer mating surface 110 sized for slidable coupling to the inner mating surface 406 of the flex adapter tube 400. The second and third electrical conductors (412, 414) may be circumferentially seated on the inner mating surface 406 and spaced apart from each other such that when the inner cannula 100 is coupled to the flex adapter tube 400, the first electrical conductor 116 is in electrical communication with both the second and third electrical conductors (412, 414).

A fourth electrical conductor 500 may be seated with the cylindrical outer mating surface 402 of the flex adapter tube 400, with the outer mating surface 402 sized and shaped appropriately for slidable coupling with the inner mating surface 208 of the shank portion 206 of the T-piece 200. The fifth and sixth electrical conductors (502, 504) may be circumferentially seated on the inner mating surface 208 and may be spaced apart appropriately so that both conductors (502, 504) may be electrically connected to the fourth electrical conductor 500 when the flex adapter tube 400 and T-piece 200 are connected.

A voltage presented at terminal A of an alarm 506 may be communicated to the second conductor 412 of the flex adapter tube 400 through terminal A' 416. If the inner cannula 100 is fully seated in the flex-adapter tube 400, the voltage will be presented to the first electrical conductor 116 of the inner cannula 100 for communication through the third electrical conductor 414 of the flex adapter tube 400 and a terminal 418 to the fifth electrical conductor 502 of the T-piece 200. If the T-piece 200 is fully seated on the outer mating surface 402 of the flex adapter tube 400, the voltage at the fifth electrical conductor 502 of the T-piece will be presented to the fourth electrical conductor 500 of the flex tube 400 for communication to the sixth electrical conductor 504 of the T-piece 200. The voltage may then be presented to Terminal B of the alarm 506 through a terminal B' 508. In this manner, if any one of the inner cannula 100 or T-piece 200 is disconnected from the flex tube 400, the voltage presented at Terminal A of the alarm 506 will not be communicated to Terminal B of the alarm 506, which may then trigger activation of the alarm's audible and/or visual signal. In an alternative embodiment, the alarm 506 may be a wireless transmitter or signal router that is in communication with a second alarm that may audible and/or visual.

Figure 6:
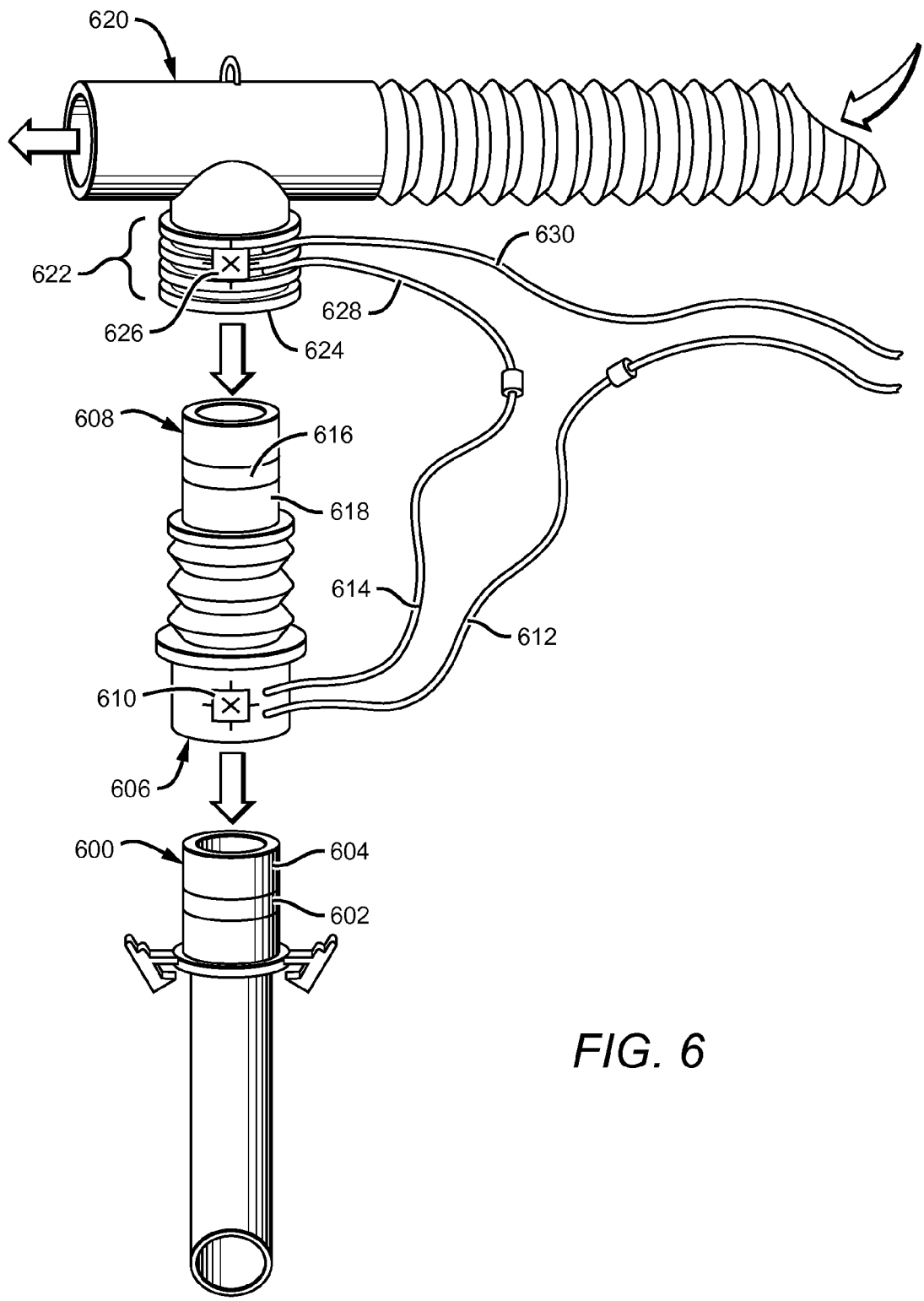
FIG. 6 depicts an exploded perspective view of another embodiment of an endotracheal tube alarm apparatus for use with a T-piece, flex adapter tube, and inner cannula where the inner cannula has a magnet in the form of a banded magnet seated circumferentially about an outer seating surface of the inner cannula.

FIG. 6 is an exploded perspective view of another embodiment of an endotracheal tube alarm apparatus for use with a T-piece, flex adapter tube, and inner cannula. In this embodiment, an inner cannula 600 may be provided with a magnet in the form of a banded magnet 602 seated circumferentially about an outer seating surface 604 of the inner cannula 600. The outer seating surface 604 may be shaped and sized appropriately for insertion into an inner seating surface 606 of a flex adapter tube 608 that has been provisioned with a Hall effect sensor 610 in electrical communication with the second and third electrical conductors (612, 614). If the flex tube 608 is fully seated on the inner cannula 600, the banded magnet 602 will be disposed adjacent to the Hall effect sensor 610 so that the Hall effect sensor 610 is enabled to sense the proximate location of the banded magnet 602 for the presentation of a suitable signal to the second and third electrical conductors (612, 614). Otherwise, if the flex tube 608 is not fully seated into the inner cannula 600, the Hall effect sensor may not sense the banded magnet 602 and will present a suitable signal to the second and third electrical conductors (612, 614) for communication to an alarm (not shown).

The flex tube 608 may also be provided with a second banded magnet 616 seated circumferentially about an outer mating surface 618 of the flex tube 608. The outer mating surface 618 may be sized and shaped appropriately for slidable coupling to a T-piece 620 that has a shank portion 622. The shank portion 622 may have an inner circumferential mating surface 624 configured to slidably receive the circumferential exterior mating surface 618 of the flex tube 608. A second Hall effect sensor 626 may be seated within the inner circumferential mating surface 624 such that when the T-piece 620 is fully seated on the flex tube 608, the second Hall effect sensor 626 is positioned in complementary opposition to the second banded magnet 616 and may communicate such position in the form of an electrical signal provided to the third and fourth electrical conductors (628, 630).

FIG. 7A is a front perspective view illustrating a ventilator tube in the form of a T-piece that is seated on an exterior circumferential ventilator tube mating surface of an inner cannula, with the resultant assembly in communication with an alarm to detect their proper connection. The T-piece 200 and inner cannula 100 may be detachably connected using a locking mechanism such as rotatable clasps 114 that extend from the T-piece 206 to ride over and then clasp the inner cannula collar 302. As illustrated in a cut-away view along the line 7B-7B, the first conductor 116, preferably in the form of a stainless steel wire, may be partially embedded (alternatively referred to as "seated") in the outer mating surface 110 of the inner cannula 100 and in electrical contact with the second and third electrical conductors (210, 212) that are partially embedded (alternatively referred to as "seated") in the inner mating surface 208 of the T-piece 200.

In another embodiment illustrated in FIG. 8, the first and second electrical conductors (212, 214) are in complementary opposition and in electrical communication with a metal bracket 800. In alternative embodiment illustrated in FIG. 9, the outer mating surface 110 may have an embedded magnet 602 for proximal detection by a Hall effect sensor 626 or by a magnetic switch (not shown).

I claim:

1. A tracheostomy tube assembly comprising:
   a trach tube inner cannula having a proximal coupler portion, a distal flexible tracheostomy portion, and a first electrical conductor;
   the first electrical conductor being on an outer mating surface of the coupler portion;
   a flexible adapter tube having a proximal sleeve end, a distal sleeve end, a flexible portion between the sleeve ends, and second, third and fourth electrical conductors;
   the second and third electrical conductors being seated in an inner mating surface of the distal sleeve end and extending out through a wall of the distal sleeve end;
   the fourth electrical conductor being on an outer mating surface of the proximal sleeve end;

a suction adapter having an oxygen flow tube portion, a shank portion communicating with and connected to the flow tube portion at an angle thereto, and fifth and sixth electrical conductors;

the fifth and sixth electrical conductors being seated in an inner mating surface of the shank portion and extending out through a wall of the shank portion;

the first, second and third electrical conductors being configured such that when the proximal coupler portion is in position in the distal sleeve end, the first electrical conductor is in electrical communication with the second and third electrical conductors;

the fourth, fifth and sixth electrical conductors being configured such that when the proximal sleeve end is in position in the shank portion, the fourth electrical conductor is in electrical communication with the fifth and sixth electrical conductors;

the conductors being configured such that with the first electrical conductor in electrical communication with the second and third electrical conductors and the fourth electrical conductor is in electrical communication with the fifth and sixth electrical conductors, the first, second, third, fourth, fifth and sixth electrical conductors are configured to form at least in part a normally-closed alarm circuit and the alarm circuit can be triggered by moving the shank portion to a disconnect position relative to the proximal sleeve end or by moving the distal sleeve end to a disconnect position relative to the proximal coupler portion; and the normally-closed alarm circuit being configured to not require connection to a mechanical ventilator.

2. The tracheostomy tube assembly of claim 1 wherein at least one of the first and second electrical conductors has an L shape.

3. The tracheostomy tube assembly of claim 1 wherein the alarm circuit includes an alarm.

4. The tracheostomy tube assembly of claim 3 wherein the alarm is in communication with the second and sixth electrical conductors via a wireless transmitter.

5. The tracheostomy tube assembly of claim 3 wherein the alarm is in communication with the second and sixth electrical conductors via at least one wire.

6. The tracheostomy tube assembly of claim 3 wherein the alarm circuit includes the second and third electrical conductors being operatively connected together, the first electrical conductor and the alarm being operatively connected together, and the sixth electrical conductor and the alarm being operatively connected together.

7. The tracheostomy tube assembly of claim 1 wherein the first electrical conductor is selected from the group consisting of: metallic wire, metallic clip, metallic strip and metallic tape.

8. The tracheostomy tube assembly of claim 1 wherein the trach tube inner cannula includes a clip configured to releasable secure the flexible adapter tube in position to the trach tube inner cannula.

9. The tracheostomy tube assembly of claim 1 wherein the trach tube inner cannula has a collar between a distal end of the proximal coupler portion and the first electrical conductor.

10. The tracheostomy tube assembly of claim 1 wherein the proximal coupler portion has a collar and a clasp on the collar configured to releasably hold the trach tube inner cannula to the flexible adapter tube with the distal flexible tracheostomy portion operatively positioned in an outer trach cannula.

* * * * *